(12) United States Patent
Viertiö-Oja et al.

(10) Patent No.: US 7,725,173 B2
(45) Date of Patent: May 25, 2010

(54) MEASUREMENT OF RESPONSIVENESS OF A SUBJECT WITH LOWERED LEVEL OF CONSCIOUSNESS

(75) Inventors: Hanna E. Viertiö-Oja, Espoo (FI); Kimmo Uutela, Helsinki (FI); Petteri Lapinlampi, Espoo (FI)

(73) Assignee: GE Healthcare Finland Oy, Helsinki (FI)

(*) Notice: Subject to any disclaimer, the term of this patent is extended or adjusted under 35 U.S.C. 154(b) by 1309 days.

(21) Appl. No.: 11/211,137

(22) Filed: Aug. 24, 2005

(65) Prior Publication Data
US 2007/0055114 A1    Mar. 8, 2007

(51) Int. Cl.
*A61B 5/04* (2006.01)
(52) U.S. Cl. ...................................... 600/544; 600/545
(58) Field of Classification Search ................. 600/544, 600/545
See application file for complete search history.

(56) References Cited

U.S. PATENT DOCUMENTS

| 3,513,834 | A  | * | 5/1970 | Takaji et al. ................ | 600/544 |
| 4,681,121 | A  | * | 7/1987 | Kobal ......................... | 600/544 |
| 5,195,531 | A  | * | 3/1993 | Bennett ....................... | 600/546 |
| 6,067,467 | A  | * | 5/2000 | John ........................... | 600/544 |
| 7,089,927 | B2 | * | 8/2006 | John et al. ............. | 128/200.24 |
| 7,198,605 | B2 | * | 4/2007 | Donofrio et al. ............ | 600/559 |
| 7,539,537 | B2 | * | 5/2009 | Hickle ......................... | 600/544 |
| 7,565,905 | B2 | * | 7/2009 | Hickle ................... | 128/203.14 |

OTHER PUBLICATIONS

*Abnormal Sleep/Wake Cycles and the Effect of Environmental Noise on Sleep Disruption in the Intensive Care Unit*, Neil S. Freedman, et al., Am J Respir Crit Care Med, vol. 163, pp. 451-457, 2001.
*A Primer for EEG Signal Processing in Anesthesia*, Ira J. Rampil, Anesthesiology, vol. 89, pp. 980-1001, 1998.

* cited by examiner

*Primary Examiner*—Patricia C Mallari
*Assistant Examiner*—Karen E Toth
(74) *Attorney, Agent, or Firm*—Andrus, Sceales, Starke & Sawall, LLP

(57) ABSTRACT

The invention relates to a method and apparatus for measuring the responsiveness of a subject with lowered level of consciousness. Physiological signal data is obtained from the subject and a first measure indicative of the level of consciousness of the subject is derived from the physiological signal data. In order to obtain an objective measure of the responsiveness of the subject and to improve the specificity of patient monitoring, a sequence of the first measure is recorded without inducing arousals in the subject and a second measure indicative of a responsiveness of the subject is determined based on the recorded sequence. The determination of the second measure may be independent of the unintentional stimuli that cause arousals in the patient or the stimuli causing such arousals in the clinical environment may be detected to find out their effect on the first measure.

21 Claims, 3 Drawing Sheets

MEASUREMENT OF RESPONSIVENESS OF A SUBJECT WITH LOWERED LEVEL OF CONSCIOUSNESS

FIELD OF THE INVENTION

The present invention relates generally to the assessment of the responsiveness of a subject with lowered level of consciousness.

BACKGROUND OF THE INVENTION

Neuromonitoring is a subfield of clinical patient monitoring focused on measuring various aspects of brain function and on changes therein caused by drugs commonly used to induce and maintain anesthesia in an operation room or sedation in patients under critical or intensive care.

Electroencephalography (EEG) is a well-established method for assessing brain activity. When measurement electrodes are attached on the skin of the skull surface, the weak biopotential signals generated in the pyramid cells of the cortex may be recorded and analyzed. The EEG has been in wide use for decades in basic research of the neural systems of the brain as well as in the clinical diagnosis of various central nervous system diseases and disorders.

Electromyography (EMG) is a method for recording electrical biopotentials of muscles. In an EMG measurement, the electrodes are attached onto the surface of the skin overlying a muscle. When a biopotential signal is recorded from the forehead of a subject, the recorded signal indicates both the activity of the facial muscles (fEMG) and the brain (EEG).

One of the special applications of the EEG, which has received attention recently, is the use of a processed EEG signal for objective quantification of the amount and type of brain activity for the purpose of determining the level of consciousness of a patient. In its simplest form, the utilization of an EEG signal allows the automatic detection of the alertness of an individual, i.e. if he or she is awake or asleep. This has become an issue of increased interest, both scientifically and commercially, in the context of measuring the depth of unconsciousness induced by anesthesia during surgery.

Another important component of balanced anesthesia is analgesia, i.e. prevention of pain reactions of a patient by administration of pain medication. Adequate analgesia reduces surgical stress and there is firm evidence that it decreases postoperative morbidity. Awareness during surgery with insufficient analgesia may lead to a post-traumatic stress disorder. Low quality pre- and intra-operative analgesia makes it difficult to select the optimal pain management strategy later on. More specifically, it may cause exposure to unwanted side effects during the recovery from the surgery. If the anesthesia is too light and involves insufficient hypnosis, it may cause traumatic experiences both for the patient and for the anesthesia personnel. From an economical point of view, if the anesthesia is too deep, it may cause increased perioperative costs through extra use of drugs and time, and extend the time required for post-operative care.

Virtually every patient being cared for in an intensive care unit (ICU), for example, receives some form of sedation. However, the control of the depth of the sedation administered to a patient is still problematic, and therefore oversedation and undersedation are both common occurrences in intensive care units. At present, monitoring the level of sedation is mainly handled by using subjective observations from the patient. Various sedation assessment scales have been developed for subjectively assessing the level of sedation, the Ramsay Score being one of the most widely used tools for this purpose.

The depth of hypnosis is not directly measurable. Therefore, drug delivery systems have to derive the level of hypnosis from a surrogate signal or from indirectly measured parameters. The most common and popular surrogate signal for this purpose is the EEG, from which several parameters may be determined. The basic reason for the insufficiency of a single parameter is the variety of drugs and the complexity of the drug effects on the EEG signal in human brains. However, during the past few years, some commercial validated devices for measuring the level of consciousness and/or awareness in clinical set-up during anesthesia or sedation have become available. Such devices, which are based on a processed EEG signal and examine the signal as a whole with its multiple features, are marketed by GE Healthcare Finland Oy, Kuortaneenkatu 2, FIN-00510 Helsinki (Entropy Index) and by Aspect Medical Systems, Inc., 141 Needham Street, Newton, Mass. 02464, U.S.A. (Bispectral Index, BIS™).

In addition to the EEG signal data, EMG signal data obtained from facial muscles (fEMG) of the forehead is used for monitoring purposes during anesthesia and intensive care. Recovering facial muscle activity is often the first indicator of the patient approaching consciousness. When this muscle activity is sensed by electrodes placed appropriately, it provides an early indication that the patient is emerging from anesthesia. Similarly, these electrodes can sense pain reactions when the anesthesia is not adequate due to inadequate analgesia. So, the EMG signals give an early warning of the arousal of the patient, and they may also be indicative of inadequate analgesia.

Several factors affect the state of the central nervous system (CNS) of an ICU patient: sedative drugs, natural sleep cycles, and brain disorders all have their effect on the EEG signal. So far, no methods exist to distinguish these components from each other to provide a clinician an overall picture of the CNS state of the patient. The development of such a method is challenging due to the non-specificity of the EEG signal. A slow wave EEG pattern, for example, may be associated with a high level of a sedative, deep natural sleep, or a severe stage of encephalopathy. Correspondingly, low EEG entropy or BIS levels may be associated with any of these causes. Furthermore, natural variations of vigilance cause high fluctuations of entropy or BIS that tend to mask any underlying information of the sedative drug effect. Therefore, the above-mentioned devices for measuring the level of (un) consciousness and/or (un)awareness are not suitable for distinguishing the different causes giving rise to the level measured.

The clinician can distinguish between the different causes by including contextual information and by stimulating the patient. For example, if a patient with a slow wave EEG has not received substantial amounts of sedative drugs and has normally functioning liver/kidneys, he cannot be too deeply sedated. If the patient in such a situation anyway does not respond to a strong external stimulus, the clinician may conclude that the patient has developed a brain disorder. To estimate the sedative drug effect and particularly to avoid too deep levels of sedation, it is recommended that some kind of stimulus-response-based scoring is regularly performed by the nursing staff. Such scores are, however, often imprecise and subjective and do not provide continuous information. Furthermore, stimulus-response-based scoring is difficult to implement in automatic monitoring.

The present invention seeks to alleviate or eliminate the above-mentioned drawbacks.

SUMMARY OF THE INVENTION

The present invention seeks to provide a novel mechanism for estimating the responsiveness of a patient with lowered level of consciousness. The lowered level of consciousness is typically induced by one or more sedative drugs, but it may also be caused by a neurological disorder. The invention further seeks to provide a mechanism that provides an objective measure of the responsiveness to be obtained automatically and improves the specificity of the patient monitoring with respect to the underlying causes giving rise to a certain level of unconsciousness.

The idea of improving the specificity of the patient monitoring by monitoring naturally occurring arousal of a patient with lowered level of consciousness is based on two discoveries. First, in a clinical environment a patient is continually exposed to some sort of unintentional stimuli that may cause arousals of different magnitudes. Second, deepening sedation of the patient tends to suppress these naturally occurring arousals, while test persons in natural sleep remain relative responsive.

In the present invention, a measure indicative of the level of (un)consciousness of a patient is first determined. For this purpose, any measure suitable for quantifying the level of (un)consciousness may be used. The measure may also be an indirect measure of the level of (un)consciousness, such as a measure based on the EMG level, movements, or opening of the eyes of the patient. Based on a recorded time series of the first measure, a second measure is then derived, which is indicative of the responsiveness of the patient. The time series of the first measure is recorded without intentionally producing arousals in the patient, i.e. all arousals that may be seen in the first measure occur naturally without proactive actions of the clinical staff. The determination of the second measure may be continuous and independent of the occurrence of the stimuli causing the arousals or the said determination may be synchronized with the occurrence of the stimuli by monitoring when such stimuli occur in the clinical environment of the patient.

Thus one aspect of the invention is providing a method for measuring the responsiveness of a subject with lowered level of consciousness The method includes the steps of obtaining physiological signal data from a subject with lowered level of consciousness and deriving a first measure from the physiological signal data, the first measure being indicative of the level of consciousness of the subject. The method further includes the steps of recording a sequence of the first measure and determining, based on the sequence, a second measure indicative of a responsiveness of the subject, wherein the method is performed without inducing arousals in the subject.

Another aspect of the invention is that of providing an apparatus for measuring the responsiveness of a subject with lowered level of consciousness. The apparatus includes means for recording a sequence of a first measure, the first measure being indicative of the level of consciousness of the subject and first calculation means for determining, based on the sequence, a second measure indicative of the responsiveness of the subject, wherein the apparatus is devoid of any stimulation means for inducing arousals in the subject.

The apparatus of the invention may be implemented as a combinatory monitor indicating both the level of consciousness and the responsiveness of the patient or as a supplementary unit of a conventional patient monitor intended for measuring the level of consciousness.

The invention enables an objective and reliable measure of the responsiveness of a patient under sedation or suffering from a neurological disorder to be obtained without additional and proactive stimulation of the patient. Thus, the measurement does not interfere with the clinical procedures.

The implementation of the determination of the second measure may vary depending on whether or not the stimuli that may cause arousals in the patient are detected. If stimulus detection is not employed, it is preferable to monitor the first measure over a time period long with respect to the typical frequency of the unintentionally occurring arousals. However, if stimulus detection is used, the second measure may be defined faster, especially if the intensity of the stimulus causing the arousal is also measured. In an extreme case, this may allow the second measure to be defined based on one arousal only.

A further aspect of the invention is that of providing a computer program product by means of which known patient monitoring devices may be upgraded and thus their applicability extended. The program product includes a first program code portion configured to record a sequence of a first measure, the first measure being indicative of the level of consciousness of the subject and a second program code portion configured to determine, based on the sequence, a second measure indicative of the responsiveness of the subject.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 6 in the appended drawings, wherein.

DETAILED DESCRIPTION OF THE INVENTION

The present invention rests on the idea that in a clinical environment a patient is continually exposed to stimuli caused by various unintentional stimulation sources. Unintentional stimulation here refers to stimulation that occurs naturally without proactive actions whose only purpose is to generate stimulus-response pairs. As discussed in Freedman, N., et al., "Abnormal Sleep/Wake Cycles and the Effect of Environmental Noise on Sleep Disruption in the Intensive Care Unit", Am. J. Respir Crit Care Med Vol 163:451-457, 2001, abrupt noise in an ICU environment causes sleep disruptions leading to arousals and awakenings. In an ICU environment, such unintentional stimuli may also be caused by various other sources external to the patient, such as lights, sounds, caregiving procedures, or the ventilation of the patient. An unintentional stimulus may also be internal, such as pain or anxiety.

In the present invention, a first measure indicative of the level of consciousness of the patient is determined. The time series of the first measure is examined to detect the raises or other changes caused by arousals resulting from unintentional stimuli. A second measure indicative of the responsiveness of the patient is then determined based on a selected sequence of the time series. The second measure may be calculated based on the frequency and/or intensity of at least one such change detected, and the number of data points in the sequence may vary depending on the implementation. The ability of the second measure to differentiate between natural sleep and unconsciousness induced by sedatives is based on the discovery that deepening sedation tends to suppress naturally occurring arousals, while test persons in natural sleep remain relative responsive. The invention therefore provides a selective mechanism for differentiating between sedation and natural sleep.

Figure 1:
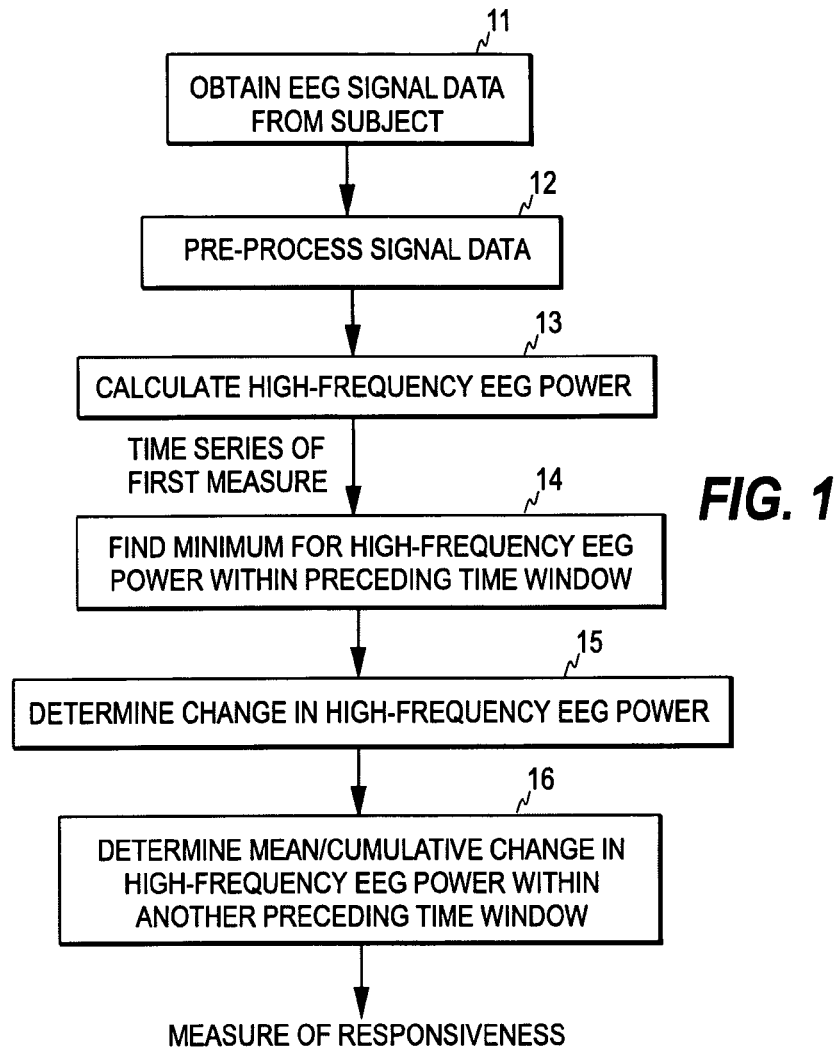
FIG. 1 is a flow diagram illustrating one embodiment of the method of the invention.

In one embodiment of the invention, the first measure represents high-frequency EEG power measured from the patient and the second measure is indicative of the occurrence of raises in the first measure. This embodiment is discussed in the following with reference to FIG. 1, which represents the continuous state of the process, i.e. it is assumed that the process has already gathered enough signal data from the patient to be able to calculate the required values over the time windows used.

The EEG signal measured from a patient (step 11) is first digitized and the sampled EEG signal is filtered to exclude high- and low-frequency artifacts (step 12). As is common in the art, the digitized signal samples are processed as sets of sequential signal samples representing finite time blocks or time windows, commonly termed "epochs". Based on the signal data, the process then calculates the current high-frequency EEG power at step 13 and stores the calculated value. The high-frequency EEG power is derived by calculating the power of the signal data in a frequency band comprising high-frequency EEG components. In this example, the said band extends from 20 Hz to 35 Hz and the length of the time window within which the power is determined corresponds to one epoch (5 seconds). The high-frequency EEG power may be derived from a power spectrum. The Fast Fourier Transform, for example, is a computationally effective algorithm for this purpose. Alternatively, the high-frequency EEG power may be calculated straight from the time-domain signal, by utilizing appropriate filters. A time series representing the first measure, which is the high-frequency EEG power in this case, is thus obtained from step 13.

The process then determines a change variable indicative of the changes in the high-frequency EEG power. For this, the process first finds the minimum high-frequency EEG power defined within a preceding time window of a predetermined length (step 14). In this example, the length of the time window from which the minimum is searched is 1 minute. The change variable is then determined by subtracting the minimum value from the current value (step 15).

The values of the change variable obtained during another, longer time window are then used to obtain a final index indicative of the mean/cumulative high-frequency EEG power changes with respect to time (step 16). The said another time window is long with respect to the typical frequency of the unintentionally caused arousals of the patient. In this example, the final index is calculated over a time window of 30 minutes, i.e. the window extends 30 minutes backwards from the current moment. Nevertheless, steps 13 to 16 may be performed for each epoch.

Figure 2:
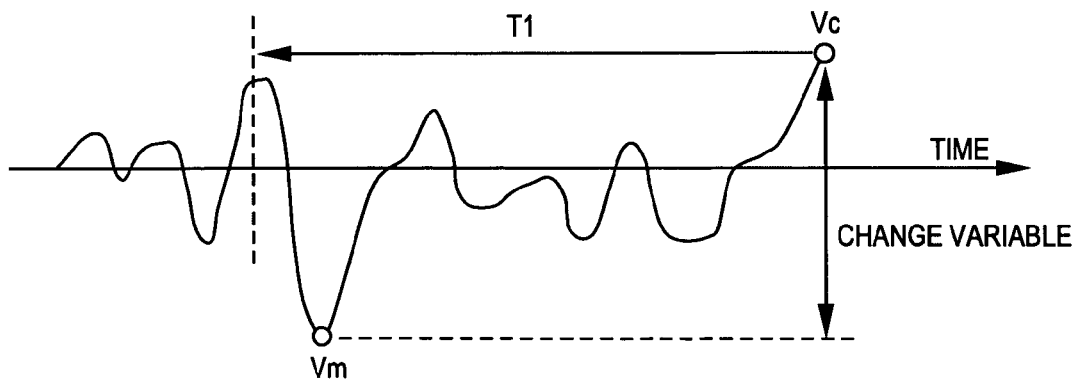
FIG. 2 illustrates the calculation of the high-frequency EEG power change in the embodiment of FIG. 1.

The determination of the change variable is illustrated in FIG. 2, in which curve 20 represents the power values obtained during the preceding time window from which the minimum is retrieved. If the current high-frequency EEG power determined at step 13 is Vc, for example, the value of the change variable corresponds to Vc−Vm. Since the absolute value of the change variable may be great, the usability of the variable may be enhanced by calculating the logarithm of the difference.

In the above embodiment, the responsiveness index R of the patient is thus determined according to equation (1) as follows:

$$R(t) = \frac{1}{T2} \int_{t-T2}^{t} \log(P_{arousal}(u))\, du, \quad (1)$$

where $P_{arousal}(u)$ $$= PEEG(u) - \min_{(u-T1) \leq v \leq u} PEEG(v),$$

and where PEEG(ti) refers to high-frequency EEG power in a short time window ti computed over the frequency range of 20 Hz to 35 Hz. In the above example, the length of this time window corresponds to one epoch (5 seconds), while T2=30 minutes and T1=1 minute, as discussed above. However, the values may change.

Due to the above subtraction, the final index does not depend on the absolute level of the background high-frequency EEG. This is an important property as the absolute high-frequency EEG power level varies substantially between different patients. For the same reason, the index is robust against stationary artifacts, such as ECG or pacemaker artifacts. On the other hand, due to the long time window the index is also relatively robust against isolated transient artifacts, such as those occurring during care procedures. Low-frequency artifacts such as eye movements obviously do not affect the index either.

The particular embodiment disclosed above uses both the amplitude and the frequency of the arousals, but the implementation of the second measure may also be based on the frequency or the amplitude of the arousals only. Requirements for artifact detection procedures depend on the choice of the frequency range used. The second measure may also indicate the frequency or the total number of substantial changes occurred within a certain preceding time window, where substantial changes refer to changes exceeding a predetermined change limit.

Figure 3:
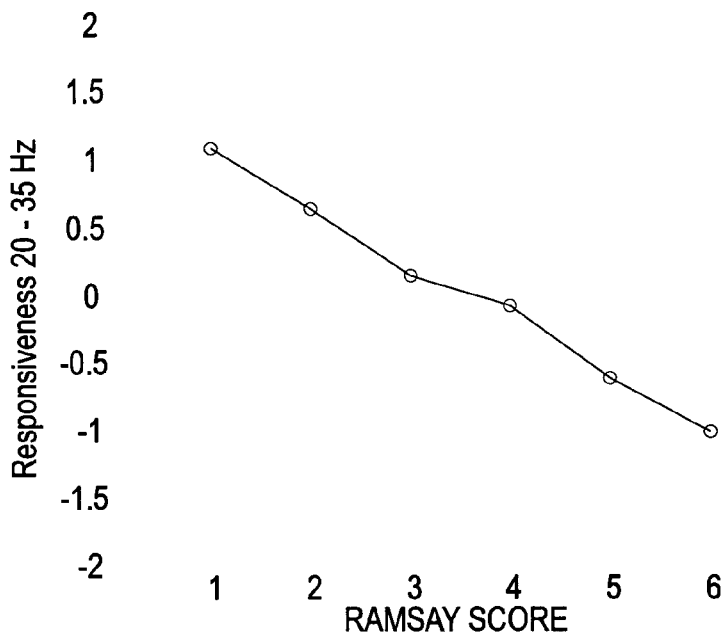
FIG. 3 shows the responsiveness index as calculated with one embodiment of the invention as a function of the Ramsay Score.

FIG. 3 illustrates the responsiveness calculated in the above-described manner as a function of the responsiveness level assessed by a clinician using the Ramsay Score. The Ramsay Score includes six levels, and the value of the responsiveness that corresponds to each level represents the mean value of the patients of the level concerned. As can be seen from the figure, the calculated index conforms to the assessment of the clinician.

Figure 4:
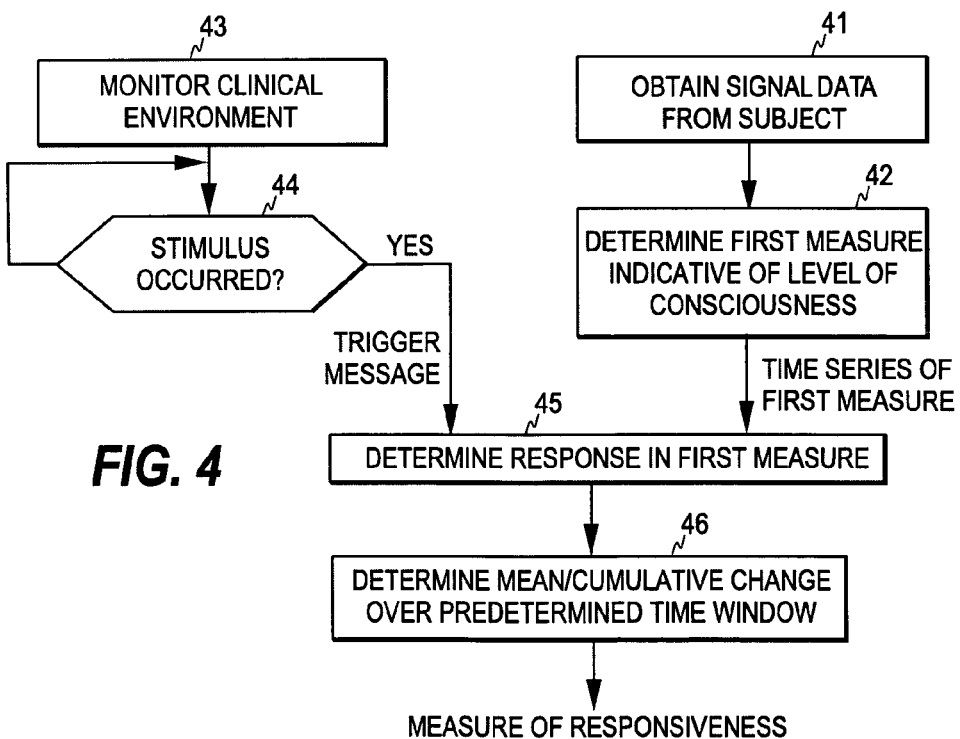
FIG. 4 illustrates another embodiment of the invention.

In the above embodiment, the values of the high-frequency EEG power are continuously examined to find the abrupt raises associated with the arousals of the patient. FIG. 4 illustrates another embodiment of the present invention, in which the determination of the responsiveness is synchronized with the natural stimuli that cause the arousals. Therefore, the first measure needs to be examined only when a stimulus occurs. In this embodiment, the first measure may be obtained as discussed above (steps 41 and 42). Concurrently, the clinical environment is monitored to detect the natural stimuli that may cause arousals of the patient (step 43 and 44). As noted above, the natural stimuli may be originated from various sources, and one or more such sources may be monitored at step 43. For example, the noise level may be recorded through a microphone and/or the airway pressure of a ventilator may be monitored to detect patient/ventilator dyssynchrony. Furthermore, if a non-invasive blood pressure monitor is used, the cuff pressurization may be used as a standard disturbance that may cause an arousal of the patient.

When detecting a disturbance that may cause an arousal of the patient, a trigger message is supplied to an analysis process (step 44/yes). The analysis process also receives the time series representing the first measure. The trigger message acts as a trigger notifying the analysis process of the occurrence of a stimulus, and the message may further include information about the type and/or magnitude (intensity) of the stimulus.

In response to the trigger message, the analysis process determines (step 45) the corresponding change in the first measure. The changes occurring within a certain time period may then be used to calculate the final index. For example, a variable indicative of the sum or mean of the changes occurring within the said time period may be calculated. The length of the period depends on the practical implementation; if the responses in the first measure are clear, the number of stimuli in the time window may be low. In an extreme case, the final index may be determined from a sequence of two measures obtained based on a single stimulus. The length of the period over which the final index is defined may thus be defined in time units or in the number of detected stimuli. If several stimulus sources are monitored, the changes caused by different sources may be weighted differently when calculating the final index.

As noted above, the EEG entropy may also be used instead of high-frequency EEG power as the first measure indicative of the level of consciousness of the patient. Instead of entropy, the evaluation of the level of consciousness may also be based on another parameter that characterizes the amount of disorder or irregularity in the EEG signal data measured from the patient. Other possible quantifications that may be used include fractal spectrum analysis, Lempel-Ziv complexity, or bispectral or multispectral analyses. A further parameter that may be employed as the first measure is the above-mentioned Bispectral Index, BIS™. The BIS involves the calculation of three parameters: Burst Suppression Ratio, Beta Ratio, and SynchFastSlow, and the resulting BIS value is a combination of the three parameters. The principles of the BIS algorithm are described in Ira J. Rampil, *A Primer for EEG Signal Processing in Anesthesia*, Anesthesiology, Vol. 89(4) October 1998, pp. 980-1002. If BIS is employed as the first measure, the present invention includes monitoring the BIS values and deriving a second measure, which is indicative of the magnitude and/or frequency of the BIS changes within a certain period. As discussed above, the second measure may indicate the mean or sum of the changes within a period of a predetermined length or the mean or sum of the changes within a period comprising a predetermined number of stimuli. The second measure may also be indicative of the rate of changes that exceed a certain limit value.

Figure 5:
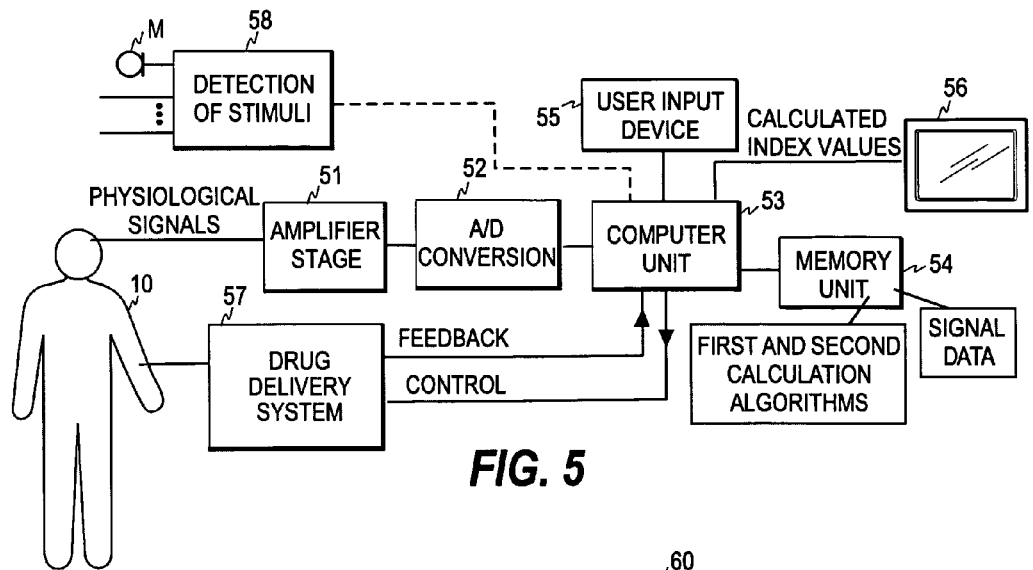
FIG. 5 illustrates one embodiment of the apparatus/system according to the invention.

FIG. 5 illustrates one embodiment of the system or apparatus according to the invention. The physiological signal(s) obtained from one or more sensors attached to a patient 10 are supplied to an amplifier stage 51, which amplifies the signal (s) before they are sampled and converted into digitized format in an A/D converter 52. The digitized signals are supplied to a computer unit 53 which may comprise one or more processors. As noted above, the signal data measured from the patient is typically EEG signal data, which is measured through electrodes applied to the forehead of the patient. The electrodes also receive high-frequency EEG signal data from the patient.

The computer unit is provided with a memory or database 54 holding the digitized signal data obtained from the sensor (s). The memory or database may also store first and second calculation algorithms that the computer unit executes in order to obtain the first and second measures, respectively. The resulting index of responsiveness may be displayed on the screen of a monitor 56. Although one computer unit or processor may perform the above steps, the processing of the data may also be distributed among different units/processors (servers) within a network, such as a hospital LAN (local area network). The apparatus of the invention may thus also be implemented as a distributed system.

If the index determination is synchronized with the occurrence of the stimuli, the apparatus/system is further provided with a detection system 58 for detecting the stimuli that may cause the arousals in the clinical environment. As discussed above, the detection system may detect one or more stimulus types, in which case it is provided with one or more detection interfaces for receiving signals indicative of the stimuli. For example, if audio stimuli occurring in the clinical environment are detected, the corresponding detection interface may be provided with a microphone M for measuring the noise level. Some of the detection interfaces may be connected to desired clinical equipment, such as to a ventilator for measuring the airway pressure for detecting patient/ventilator dyssynchrony or to a blood pressure cuff for detecting when the cuff is pressurized.

The computer unit may further act as a controlling entity controlling the administration of the drugs from the delivery system 57 to the patient. The computer unit may also supply the values of the responsiveness index to another computer unit or microprocessor (not shown), which then acts as the controlling entity controlling the drug delivery system. The said controlling entity may be provided with the control data needed for the administration, such as the pharmacodynamic and pharmacokinetic properties of the drugs to be administered. The drug delivery system may comprise separate delivery units for one or more drugs to be administered, such as a delivery unit for an analgesic drug and/or a delivery unit for a hypnotic drug.

The computer unit may also act as a decision-support tool for the physician, such as an anesthesiologist, who may control the operation of the drug delivery system through an appropriate user input device 55, such as a keyboard or a bar code reader. Various parameters possibly needed in the calculation of the first and second measures may also be supplied through the input device, if the computer unit has no access to such data.

A conventional patient monitor intended for measuring the level of consciousness may also be upgraded to enable the monitor to determine the responsiveness index of the invention. Such an upgrade may be implemented by delivering to the patient monitor a plug-in software module that enables the device to calculate the responsiveness index based on the time series of the first measure defined in the device. The software module may be delivered, for example, on a data carrier, such as a CD or a memory card. As discussed above, the patient monitor may be an entropy-based monitor or a BIS monitor, for example. The plug-in software module has access to the time series of the entropic indicators or the BIS values, whereby it may calculate the responsiveness index in the above-described manner.

The software module may also comprise a new version of the software, which replaces the existing software of the patient monitor.

Figure 6:
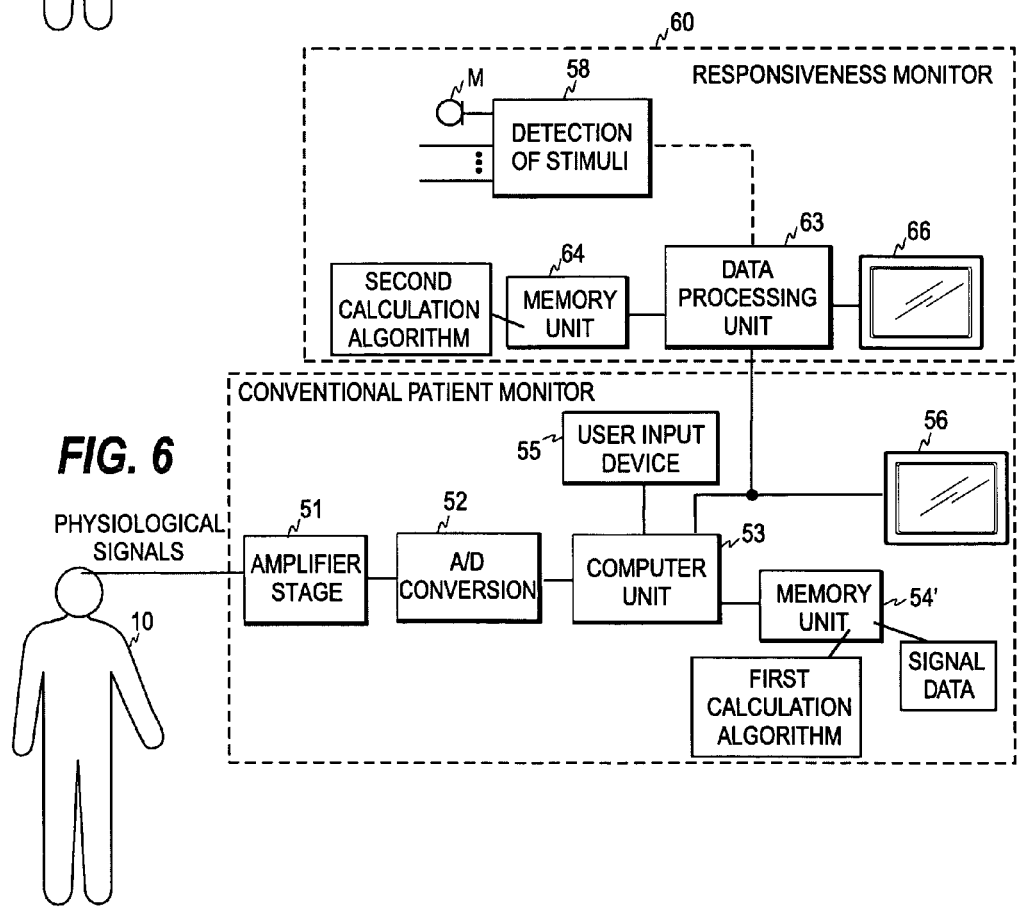
FIG. 6 illustrates another embodiment of the apparatus/system of the invention.

A responsiveness monitor of the invention may also be implemented as a separate module connectable to a conventional patient monitor intended for measuring the level of consciousness. As is shown in FIG. 6, such a responsiveness monitor 60 may comprise a data processing unit 63 which receives the time series of the first measure from the conventional patient monitor and derives the second measure from the said time series. The responsiveness monitor may comprise a display of its own for displaying the calculated responsiveness index to the user, and it may optionally include the above-described detection system 58.

Although the invention was described above with reference to the examples shown in the appended drawings, it is obvious that the invention is not limited to these, but may be modified by those skilled in the art without departing from the scope of the invention.

The invention claimed is:

1. A method for measuring the responsiveness of a subject with lowered level of consciousness, the method comprising the steps of:
   obtaining physiological signal data from a subject with lowered level of consciousness;
   deriving, in a computer unit, a first measure from the physiological signal data, the first measure being indicative of the level of consciousness of the subject;
   recording, in a computer unit, a sequence of the first measure; and
   based on the sequence, determining, in a computer unit, a second measure indicative of a responsiveness of the subject,
   wherein the method is performed without inducing arousals in the subject.

2. A method according to claim 1, wherein the determining step includes the sub-steps of:
   determining a third measure indicative of a change in the first measure, wherein the third measure is determined substantially at regular intervals; and
   deriving the second measure from a sequence of the third measure, the sequence of the third measure containing values of the third measure determined within a first preceding time window of a predetermined length.

3. A method according to claim 2, wherein the deriving sub-step includes deriving the second measure for each third measure.

4. A method according to claim 2, wherein the determining sub-step includes finding a minimum value of the first measure from a second preceding time window of a predetermined length and deriving each value of the third measure from the difference between current value of the first measure and the minimum value found, wherein the sequence of the first measure contains the second preceding time window.

5. A method according to claim 2, wherein the deriving sub-step includes calculating a variable indicative of the sum of the sequence of the third measure.

6. A method according to claim 2, wherein the deriving sub-step includes calculating a variable indicative of the mean of the sequence of the third measure.

7. A method according to claim 6, wherein the determining sub-step includes finding a minimum value of the first measure from a second preceding time window of a predetermined length and deriving each value of the third measure as the logarithm of the difference between current value of the first measure and the minimum value found.

8. A method according to claim 2, wherein the deriving sub-step includes determining the frequency of substantial changes in the first measure within the first preceding time window.

9. A method according to claim 2, wherein the deriving sub-step includes determining the total number of substantial changes in the first measure within the first preceding time window.

10. A method according to claim 1, wherein
    the obtaining step includes obtaining EEG signal data from the subject; and
    the deriving step includes deriving the first measure, in which the first measure is indicative of power in a high-frequency band of the EEG signal data.

11. A method according to claim 1, wherein
    the obtaining step includes obtaining EEG signal data from the subject; and
    the deriving step includes deriving the first measure, in which the first measure is indicative of an entropy of the EEG signal data.

12. A method according to claim 1, wherein
    the obtaining step includes obtaining EEG signal data from the subject; and
    the deriving step includes deriving the first measure, in which the first measure is indicative of the Bispectral Index (BIS™) of the EEG signal data.

13. A method according to claim 1, wherein
    the obtaining step includes obtaining EMG signal data from the subject; and
    the deriving step includes deriving the first measure, in which the first measure is indicative of power of the EMG signal data.

14. A method according to claim 1, further comprising a step of detecting a stimulus produced by at least one predetermined stimulus source.

15. A method according to claim 14, wherein the detecting step includes measuring noise level.

16. A method according to claim 14, wherein the detecting step includes detecting a predetermined clinical procedure.

17. A method according to claim 14, wherein the detecting step includes measuring an intensity of the stimulus.

18. A method according to claim 14, wherein determining step includes the sub-steps of:
    measuring a change caused by the stimulus in the first measure, wherein the stimulus is produced by at least one of the at least one predetermined stimulus source; and
    determining the second measure based on the change measured.

19. A method according to claim 14, wherein the determining step includes the sub-steps of:
    measuring changes caused by a plurality of stimuli in the first measure, wherein the plurality of stimuli is produced by at least one of the at least one predetermined stimulus source; and
    determining the second measure based on the changes measured.

20. A method according to claim 19, wherein the measuring sub-step includes measuring the changes over a time period, the length of the time period being measured in a predetermined manner.

21. A method according to claim 19, wherein determining sub-step includes defining the mean value of the changes measured.

* * * * *